United States Patent [19]

Hruza nee Sanderson et al.

[11] 4,024,190
[45] May 17, 1977

[54] NOVEL LOWER ALKENALS

[75] Inventors: Anne Hruza nee Sanderson, Bricktown; William L. Schreiber, Jackson, both of N.J.; Michel van Praag, Tilburg, Netherlands; Alan O. Pittet, Atlantic Highlands; William J. Evers, Red Bank, both of N.J.

[73] Assignee: International Flavors & Fragrances Inc., New York, N.Y.

[22] Filed: May 5, 1976

[21] Appl. No.: 683,293

Related U.S. Application Data

[63] Continuation-in-part of Ser. No. 383,578, July 30, 1973, Pat. No. 3,970,701.

[52] U.S. Cl. ............................ 260/601 R; 426/534; 252/522
[51] Int. Cl.² ..................... C07C 47/02; C11B 9/00
[58] Field of Search .............................. 260/601 R

[56] References Cited

UNITED STATES PATENTS 3,970,701  7/1976  Sanderson ..................... 260/601 R

OTHER PUBLICATIONS

Chuche et al., "Chem. Abstract," vol. 69, p. 76535y (1968).
Sucrow "Chem. Abstracts," vol. 68 (1968), p. 5901g.
Sucrow, "Chem. Abstracts," vol. 74 (1971), p. 52962n.

*Primary Examiner*—James O. Thomas, Jr.
*Assistant Examiner*—W. B. Lone
*Attorney, Agent, or Firm*—Arthur L. Liberman; Harold Haidt; Franklin D. Wolffe

[57] ABSTRACT

Novel lower 2-alkyldene-3-alkenals having the generic formula:

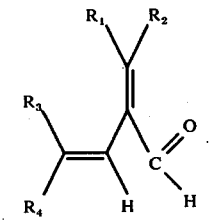

wherein one of $R_1$ and $R_2$ is hydrogen and the other is methyl, and one of $R_3$ and $R_4$ is hydrogen and the other is an alkyl group having two or four carbon atoms, but specifically, selected from the group consisting of:
  cis-2-ethylidene-trans-3-hexenal;
  cis-2-ethylidene-cis-3-hexenal;
  trans-2-ethylidene-trans-3-hexenal;
  trans-2-ethylidene-6-methyl-cis-3-heptenal; and
  trans-2-ethylidene-6-methyl-trans-3-heptenal
such alkenals being useful in altering, augmenting or enhancing organoleptic properties of foodstuffs, perfume compositions, perfumed articles and tobaccos.

7 Claims, No Drawings

NOVEL LOWER ALKENALS

This application is a continuation-in-part of U.S. Pat. application for Letters Patent Ser. No. 383,578, filed on July 30, 1973, now U.S. Pat. No. 3,970,701.

BACKGROUND OF THE INVENTION

The present invention provides novel alkylidene alkenals useful for altering the organoleptic properties of consumable materials such as foodstuffs, tobacco products, and perfumes.

U.S. Pat. No. 3,463,818 shows unsaturated aldehydes having various floral odors and processes for preparing such compounds. Japanese published application 72/43526 shows the synthesis of terpene derivatives having orangelike odors, and hexadienal derivatives are shown. Wiemann et al, Memoires Presentes Soc. Chim., 1966, 1760, describe nuclear magnetic residence studies on some conjugated dienals, and a number of these compounds, including 2-ethylidene-3-pentenal are shown. 2-Propenyl-2-pentenal is mentioned in Chem. Abstracts 35, 6238.

West German published application 1,951,883 is said in Chem. Abstracts 75, 5246 to show preparation of dienals useful as perfumes. Tiffeneau et al, Comptes Rend. 204, 590 show the preparation of 2-alkylidene-3-butenal.

U.S. Pat. Nos. 3,272,873; 3,453,317; and 3,493,619 show processes for preparing unsaturated aldehydes or for treating such aldehydes. U.S. Pat. No. 3,520,936 shows production of an unsaturated aldehyde, and U.S. Pat. No. 3,542,878 shows an aldol condensation using a tin catalyst.

Odiger et al Annalen 682 58; Corey et al, J. Am. Chem. Soc. 90, 6816; and Wittig et al, Chem. Ber. 94 676 show alklidenylation reactions utilizing phosphorus compounds.

THE INVENTION

The present invention provides novel 2-alkylidene-3-alkenals useful for altering the organoleptic properties of consumable materials. Briefly, the novel compounds are 2-alkylidene-3-alkenals having the formula:

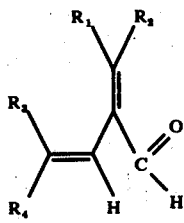

wherein one of $R_1$ and $R_2$ is hydrogen and the other is methyl, and one of $R_3$ and $R_4$ is hydrogen and the other is an alkyl group containing two or four carbon atoms; and more specifically, the compounds:
  cis-2-ethylidene-trans-3-hexenal;
  cis-2-ethylidene-cis-3-hexenal;
  trans-2-ethylidene-trans-3-hexenal;
  trans-2-ethylidene-6-methyl-cis-3-heptenal; and
  trans-2-ethylidene-6-methyl-trans-3-heptenal.

Thus, the alkyl groups contemplated according to the present invention are lower alkyl groups. Preferably the alkyl groups represented by $R_3$ and $R_4$ are ethyl or isobutyl.

It will be understood from the present disclosure that several "cis-trans" isomers are possible as a result of the presence of substituents on the carbon atoms surrounding the carbon-carbon double bond of the alkenal chain as well as the alkylidene moiety and such isomers are contemplated herein.

As an instant, a preferred alkenal is 2-ethylidene-6-methyl-cis-3-heptenal (primarily trans-2-ethylidene-6-methyl-cis-3-heptenal):

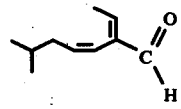

which has a green, floral, slightly cucumber top fragrance note with a twig-like undertone particularly suiting it for use in fragrance compositions.

Trans-2-ethylidene-trans-3-hexenal,

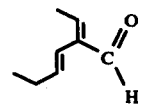

has an odor noticeably different from the trans-2-ethylidene-cis-3-hexenal having more of a musty, harsher nuance, but also a citrus, albedo-like character (which has a citrus, albedo-like character, also at 1 ppm a hydrogen cyanide-like, sweet, almond, marzipan-like aroma and taste; at 2 ppm a characteristic apricot kernel, hydrogen cyanide-like, marzipan aroma and taste; at 5 ppm a characteristic apricot kernal, hydrogen cyanide-like, marzipan aroma and taste and in addition green and black cherry notes) having more of a musky, harsher nuance, but also a citrus albedo-like character.

Cis-2-ethylidene-cis-3-hexenal,

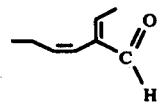

in admixture with trans-2-ethylidene-cis-3-hexenal and the diethyl acetal of cis-2-ethylidene-cis-3-hexenal in the following proportion:

| | |
|---|---|
| Cis-2-ethylidene-cis-3-hexenal | 70% |
| Trans-2-ethylidene-cis-3-hexenal | 20% |
| Diethyl acetal of cis-2-ethylidene-cis-3-hexenal | 10% | at 0.5 ppm imparts a "juicier" note to organe drink flavor. The taste has dominating fresh green notes with light, spicy backnotes. It has a delicate, green, twiggy, leafy, fruity, aroma note with a natural cinnamon note on dry-out.

The 2-alkylidene-3-alkenal derivatives and mixtures thereof according to the present invention can be used to alter, vary, fortify, modify, enhance, or otherwise improve the organoleptic properties, including flavor and/or aroma, of a wide variety of materials which are ingested, consumed, or otherwise organoleptically sensed.

The term "alter" in its various forms will be understood herein to mean the supply or imparting a flavor character or note to an otherwise bland, relatively tasteless substance, or augmenting an existing flavor characteristic where the natural flavor is deficient in some regard, or supplementing the existing flavor or aroma impression to modify the organoleptic character. The materials which are so altered are generally referred to herein as consumable materials.

The term "enhance" is used herein to mean the intensification of a flavor or aroma characteristic or note without the modification of the quality thereof. Thus, "enhancement" of a flavor or aroma means that the enhancement agent does not add any additional flavor note.

Such 2-alkylidene-3-alkenal derivatives are accordingly useful in flavoring compositions. Flavoring compositions are herein taken to mean those which contribute a part of the overall flavor impression by supplementing or fortifying a natural or artificial flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus, foodstuffs includes meats, gravies, soups, convenience foods, malt and other alcoholic or non-alcoholic beverages, milk and dairy products, nut butters such as peanut butter and other spreads, seafoods including fish, crustaceans, mollusks and the like, candies, breakfast foods, baked goods, vegetables, cereals, soft drinks, snack foods, dog and cat foods, other veterinary products, and the like.

The term "tobacco" will be understood herein to mean natural products such as, for example, burley, Turkish tobacco, Maryland tobacco, flue-cured tobacco and the like including tobacco-like or tobacco-based products such as reconstituted or homogenized leaf and the like, as well as tobacco substitutes intended to replace natural tobacco, such as lettuce and cabbage leaves and the like. The tobaccos and tobacco products include those designed or used for smoking such as in cigarette, cigar, and pipe tobacco, as well as products such as snuff, chewing tobacco, and the like.

When the 2-alkylidene alkenal derivatives according to this invention are used in a flavoring composition, they can be combined with conventional flavoring materials or adjuvants. Such co-ingredients or flavoring adjuvants are well known in the art for such use and have been extensively described in the literature. Apart from the requirement that any such adjuvant material be ingestibly acceptable, and thus non-toxic or otherwise non-deleterious, conventional materials can be used and broadly include other flavor materials, vehicles, stabilizers, thickeners, surface active agents, conditioners, and flavor intensifiers.

The 2-alkylidene alkenal derivatives, or the compositions incorporating them, as mentioned above, can be combined with one or more vehicles or carriers for adding them to the particular product. Vehicles can be edible or otherwise suitable materials such as ethyl alcohol, propylene glycol, water, and the like. Carriers include materials such as gum arabic, carrageenan, other gums, and the like. The alkenal compounds according to this invention can be incorporated with the carriers by conventional means such as spray-drying, drum-drying, and the like. such carriers can also include materials for coacervating the alkylidene alkenal derivatives (and other flavoring ingredients, as present) to provide encapsulated products. When the carrier is an emulsion, the flavoring composition can also contain emulsifiers such as mono- and diglycerides of fatty acids and the like. With these carriers or vehicles, the desired physical form of the composition can be prepared.

When the derivatives are used to treat tobacco products for example, the additive can be applied in a suitable manner, as by spraying, dipping, or otherwise. They can be applied during the "casing" or final spray treatment of the tobacco, or they can be applied at some earlier stage of curing or preparation. The quantity of alkylidene alkenal derivatives or mixtures thereof utilized should be sufficient to impart the desired flavor characteristic to the product, but on the other hand, the use of an excessive amount of the derivative is not only wasteful and uneconomical, but in some instances too large a quantity may unbalance the flavor or other organoleptic properties of the product consumed. The quantity used will vary depending upon the ultimate foodstuff, tobacco product, or other consumable product; the amount and type of flavor initially present in the product; the further process or treatment steps to which the product will be subjected; regional and other preference factors; the type of storage, if any, to which the product will be subjected; and the preconsumption treatment, such as baking, frying, and so on, given to the product by the ultimate consumer. Accordingly, the terminology "effective amount" and "sufficient amount" is understood in the context of the present invention to be quantitatively adequate to alter the flavor of the foodstuff, tobacco, or other consumable material.

It is accordingly preferred that the ultimate compositions contain from about 0.02 parts per million (ppm) to about 150 ppm of 2-alkylidene alkenal derivative or derivatives. More particularly, in food compositions it is desirable to use from about 0.05 ppm for enhancing flavors and in certain preferred embodiments of the invention, from about 0.2 to 50 ppm of the derivatives are included to add positive flavors to the finished product. On the other hand, tobacco compositions can contain as little as 0.5 ppm and as much as 250 ppm depending upon whether a cigarette tobacco, a pipe tobacco, a cigar tobacco, a chewing tobacco, or snuff is being prepared. All parts, proportions, percentages, and ratios herein are by weight unless otherwise indicated.

The amount of 2-alkylidene alkenal material or materials to be utilized in flavoring compositions can be varied over a wide range depending upon the particular quality to be added to the foodstuff, tobacco, or other consumable material. Thus, amounts of one or more derivatives according to the present invention from about 2 ppm up to 80 or 90 percent can be incorporated in such compositions. It is generally found to be desirable to include from about 10 ppm to about 0.1 percent of the derivatives in such compositions.

The 2-alkylidene alkenal derivatives of this invention are also useful individually or in admixture as fragrances. They can be used to contribute various fruity, woody, or floral fragrances. As olfactory agents, the derivatives of this invention can be formulated into or used as components of a "perfume composition".

A perfume composition is composed of a small but effective amount of an 2-alkylidene-3-alkenal derivative according to this invention and an auxiliary perfume ingredient, including, for example, alcohols, aldehydes, ketones, nitriles, esters, and frequently hydrocarbons which are admixed so that the combined odors of the individual components produce a pleasant or desired fragrance. Such perfume compositions usually contain (a) the main note or the "bouquet" or foundation-stone of the composition; (b) modifiers which round-off and accompany the main note; (c) fixatives which include odorous substances which lend a particular note to the perfume throughout all stages of evaporation, and substances which retard evaporation, and (d) top-notes which are usually low-boiling fresh-smelling materials.

It will thus be apparent that the derivatives according to the present invention can be utilized to alter the sensory properties, particularly organoleptic properties such as flavor and/or fragrance of a wide variety of consumable materials.

The novel 2-alkylidene alkenals of the present invention can readily be prepared by a number of reaction routes, as will be apparent to those skilled in the art from the present disclosure. Thus, they can be prepared by reacting an alkyl metallo acetylide with a dialkoxyacetonitrile to form an imine salt, hydrolyzing the imine salt to form 1,1-dialkoxy-3-alkyn-2-one, treating the 1,1-dialkoxy-3-alkyne-2-one with an alkylidene triphenyl phosphorane, hydrolyzing the 1,1-dialkoxy-2-alkylidene-3-alkyne so formed in acidic aqueous solution to provide 2-alkylidene-3-alkynal, and reducing the triple bond to a double bond as by hydrogenation to obtain the novel 2-alkylidene-3-alkenal.

It is significant that hydrogenation of the 1,1-dialkoxy-3-alkyne-2-one will yield, primarily, the isomer 1,1-dialkoxy-cis-3-alkene-2-one which is then isomerized to the 1,1-dialkoxy-trans-3-alkene-2-one using an appropriate cis-trans isomerization reagent such as a mixture of acetic acid and sodium iodide or potassium iodide (Preferred concentration range of alkali metal iodide in acetic acid, from 0.5% up to 2% by weight). It should further be noted that hydrolysis of the 1,1-dialkoxy-2-alkylidene-trans-3-alkenal produced as the result of reaction of the tri-substituted alkylidene phosphorane with the 1,1-dialkoxy-3-trans-alkene-2-one will yield a mixture of cis-2-alkylidene-trans-3-alkenal and trans-2-alkylidene-trans-3-alkenal. The cis-2-alkylidene-trans-3-alkenal in the mixture may then be specifically isomerized to the trans-2-alkylidene-trans-3-alkenal (thus creating a material containing only the one isomer, to wit: trans-2-alkylidene-trans-3-alkenal) by means of an appropriate cis-trans isomerization agent such as a mixture of acetic acid and an alkali metal iodide such as sodium iodide or potassium iodide.

Alternatively, the compounds described herein can be produced by a process comprising the steps of: (1) reacting an aliphatic α,β-unsaturated aldehyde with an halogen to provide the corresponding α-halo aldehyde derivative; (2) either (i) reacting the said α-halo aldehyde derivative with an alkyl magnesium halide (Grignard reagent) hydrolyzing the resulting product to form a hydroxyhaloalkene and dehydrating the resulting hydroxyhaloalkene to form a trans halo alkadiene or (ii) reacting the said α-halo aldehyde derivative with a trisubstituted alkylidene phosphorane or an alkylidene phosphorous triamide to provide a mixture of cis and trans halo alkadienes having structures:

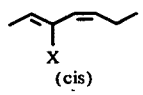
X
(cis)

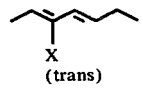
X
(trans)

(3) either (i) treating either the mixture of said halo alkadiene isomers or said trans halo alkadiene with a metal such as magnesium thereby forming an organometallic reagent and reacting the said organometallic reagent so formed with a trialkyl orthoformate to yield an acetal which is then hydrolyzed with acid to yield the desired alkylidene-trans-alkenal or (ii) reacting the mixture of halo alkadiene isomers with an alkyl lithium to form a lithioalkadiene (mixture of isomers) and then reacting said organometallic reagent with a dialkyl formamide or an aryl alkyl formamide followed by acid hydrolysis thus forming a mixture of 2-alkylidene-cis-3-alkenal and alkylidene-trans-3-alkenal or (iii) physically separating the cis halo alkadiene from the trans halo alkadiene and then reacting each isomer independently with an alkyl lithium to form lithio alkadienes and then reacting each of said lithio alkadienes with a dialkyl formamide or an aryl alkyl formamide followed by acid hydrolysis forming, separately, an alkylidene-trans-alkenal and an alkylidene-cis-alkenal.

In these reactions, the various alkyl and alkylidene substituents are chosen to provide the desired final compounds. The cis-trans isomer ratios are controlled by suitable reaction conditions and/or separation techniques.

The intermediate and/or final products obtained can be purified or isolated by conventional purification after appropriate washing, neutralizing and/or drying as appropriate. Thus, such products can be purified and/or isolated by distillation, steam distillation, vacuum distillation, extraction, preparative chromatographic techniques, and the like.

The following examples are given to illustrate embodiments of the invention as it is presently preferred to practice it. It will be understood that these examples are illustrative, and the invention is not to be considered as restricted thereto except as indicated in the appended claims.

EXAMPLE I

Preparation of 2-Ethylidene-6-methyl-cis-3-heptenal

A solution of 5.40 g of isobutylacetylene in 50 ml of diethyl ether is treated with 30 ml of 2.2 N n-butyllithium in hexane at −20° C, and after several minutes the resulting solution is treated with 8.50 g of diethoxyacetonitrile and then warmed slowly to room temperature. After about 1.5 hours the dark mixture is cooled and brought to a pH of about 2 with ten percent sulfuric acid.

The layers are then separated and the organic layer is washed successively with water and saturated aqueous sodium bicarbonate solution and then dried over sodium sulfate. Evaporation of the solvent provides 4.6 g of a dark oil, shown by IR and NMR to contain 1,1-diethoxy-6-methyl-3-heptyn-2-one.

A solution of ethylidenetriphenylphosphorane is prepared by admixing 17.0 g of ethyltriphenylphosphonium bromide with 20 ml of 2.3 N phenyllithium in a 70:30 benzene: ether vehicle. This is added to the heptynone, with the temperature being held below 30° C with cooling.

A few minutes after the addition is completed, the mixture is partitioned between water and ether phases. The layers are separated, and the organic phase is dried over sodium sulfate and evaporated. The residue is dissolved in hexane and filtered to remove triphenylphosphine oxide. After evaporation of the hexane, the 10.4 g of crude acetal obtained is hydrolyzed to the acetylenic aldehyde in 30 percent aqueous acetic acid.

The crude aldehyde is isolated by partitioning between water and ether; the ether layer is washed successively with water and saturated aqueous sodium carbonate and dried over sodium sulfate; and the solvent is evaporated. The residue is hydrogenated in hexane solution over 1.0 g of Lindlar catalyst (5 percent palladium on calcium carbonate poisoned with lead acetate) at a pressure of about four atmospheres.

The mixture is filtered and the solvent is evaporated to provide 3.8 g of dark oil from which the 2-ethylidene-6-methyl-cis-3-heptenal is isolated by preparative GLC.

The NMR analysis of the resulting material is as follows:

| | | |
|---|---|---|
| 0.82 ppm (d) | Methyl protons of isopropyl group | 6H |
| 2.30–1.24 (m) | Methine & methylene protons | |
| | } | 6H |
| 1.88 (d) 5.80 (m) | =C—CH$_3$ \| HC=CH | 2H |
| 6.60 (q) | H \| Me—CH | 1H |
| 9.38 (s) | \| HC=O | 1H |

The IR analysis is as follows:
762cm$^{-1}$, 1078, 1205, 1380, 1470, 1690, 2940.
The Mass Spectral analysis is as follows:

| m/e | Relative Intensity |
|---|---|
| 27 | 58[3] |
| 29 | 40 |
| 39 | 51[5] |
| 41 | 70[2] |
| 43 | 45[6] |
| 53 | 31 |
| 67 | 33 |
| 81 | 52[4] |
| 95 | 37 |
| 109 | 100[1] |
| 150 (Parent Peak) | 8 |

The material

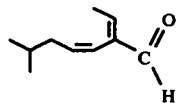

has a green, floral, violet, slightly cucumber fragrance.

EXAMPLE II

Preparation of 1,1-Dimethoxy-cis-3-hexene-2-one

Six grams of the 1,1-dimethoxy-3-hexyne-2-one (of Example I) is stirred under hydrogen gas at one atmosphere in 40 ml hexane containing 0.6 g Lindlar catalyst (palladium on calcium carbonate poisoned with lead acetate) and 4.0 g quinoline. The reaction is terminated when one percent of the starting material (1,1-dimethoxy-3-hexyne-2-one) remains.

The mixture is filtered and the quinoline washed out with dilute aqueous hydrochloric acid. The organic layer is washed with saturated aqueous sodium bicarbonate and then brine; the solvent is evaporated. GLC and NMR of the crude material shows the product is substantially 1,1-dimethoxy-cis-3-hexene-2-one having the structure:

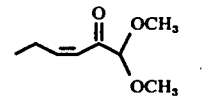

EXAMPLE III

Preparation of 1,1-Dimethoxy-trans-3-hexene-2-one

The crude product produced in Example II is disolved in 6 ml of acetic acid with 0.1 g of sodium iodide. By GLC on Carbowax(polyethylene glycol) it is clear that the 1,1-dimethoxy-cis-3-hexene-2-one is converted to a new material of later retention time. After one-half hour less than 5 percent of "cis" material remains.

The material is isolated by partitioning between water and ether, washing the ether layer successively with aqueous sodium bicarbonate and brine and then drying over 4A molecular sieves. Evaporation of the solvent provides 5.0 g of yellow oil. NMR and GLC indicate essentially all trans material having the structure:

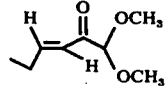

EXAMPLE IV

Ethyltriphenylphosphonium bromide (3.71 g) and 6.3 ml of 1.6 N n-butyl lithium are mixed in ether solution and 1.58 g of the 1,1-dimethoxy-trans-3-hexene-2-one of Example II is added, while keeping the internal temperature below 30° C. After a few minutes the mixture is filtered and the solvent evaporated. A small amount of solid is present so the residue is dissolved in isopentane, filtered, and again evaporated to give 1.10 g of a yellow-orange oil.

GLC and NMR indicate that presence of two acetals of 2-ethylidene-trans-3-hexenal: cis and trans isomers at the ethylidene group namely: cis-2-ethylidene-trans-3-hexenal dimethyl acetal and trans-2-ethylidene-trans-3-hexenal dimethyl acetal. The acetal material is dissolved in 2 ml water and 3 ml acetic acid with a small amount of sodium iodide isomerization reagent. After a few minutes GLC shows complete hydrolysis. (In the absence of sodium iodide a mixture of cis and trans ethylidene isomers of the aldehydes is obtained).

The produce is isolated by partitioning between water and ether. The organic layer is washed successively with water, aqueous sodium bicarbonate, and aqueous sodium chloride and finally evaporated to give 0.70 g of an orange oil. The major peak (80%), isolated by preparative GLC is trans-2-ethylidene-trans-hexenal having the structure:

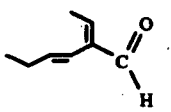

EXAMPLE V

Preparation of (Z)-2-Ethylidene-(Z)-3-hexenal (or cis-2-ethylidene-cis-3-hexenal)

A slurry of 4.20 g ethyltriphenylphosphoniumiodide in 30 ml ether is mixed with 4.3 ml 2.3N phenyllithium in benzene: ether to provide a deep orange solution. 1,1-Dimethoxy-3-hexyne-2-one as obtained in Example I (1.56 g) is added, keeping the temperature below 30°, and the resulting mixture is stirred one hour. Water and more ether are added, the mixture is filtered the layers separated, and the organic layer washed with brine and then evaporated.

The residue is dissolved in isopentane, filtered, and evaporated to give 2.0 g of orange-colored oil. The crude product is hydrogenated at about one atmosphere pressure in 10 ml pyridine over 0.2 g palladium on barium sulfate and the material is re-isolated by partitioning between ether and water. The organic layer is washed several times with water and then saturated aqueous sodium chloride.

After removal of solvent there is a red-orange oil which contains some pyridine. The major product is isolated by preparative GLC. The trapped material (140 mg.) is hydrolyzed by stirring it in ether solution with 5 percent sulfuric acid. After 1½ hours at room temperature the mixture is worked up by separating the layers, washing the ether layer with aqueous sodium bicarbonate followed by saturated aqueous sodium chloride and evaporating through a Vigreux column to give 110 mg of a very pale green oil with a fresh "green" aroma.

By GLC it is found to contain 10 percent of the acetal, and by NMR, to contain 20 percent of the stable isomer. The major product is the cis-2-ethylidene-cis-3-hexenal isomer with the structure:

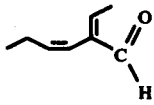

EXAMPLE VI

Tobacco Flavor

Two tobacco flavor formulations are prepared by admixing:

| Formula A | |
|---|---|
| Ingredients | Parts |
| Pyroligneous acid | 10.00 |
| Solid extract cornsilk | 18.00 |
| Solid extract foenugreek | 3.50 |
| Vanillin | 0.15 |
| Cyclotene | 0.05 |
| 2-Ethyl-3-methylpyrazine | 0.10 |
| Methyl heptynyl carbonate | 0.05 |
| Eugenol | 0.10 |
| Trans-2-ethylidene-trans-3-hexenal (Produced by Example IV) | 1.00 |

-continued

| Formula A | |
|---|---|
| Ingredients | Parts |
| Propylene Glycol | 67.05 |

| Formula B | |
|---|---|
| Ingredients | Parts |
| 2-Ethyl-3-methylpyrazine | 0.10 |
| 2-Methylvaleric acid | 1.00 |
| Methyl heptynyl carbonate | 0.25 |
| Pyroligneous acid | 10.00 |
| Cis-2-Ethylidene-cis-3-hexenal (Produced by Example V | 1.00 |
| Vanillin | 0.02 |
| Solid extract foenugreek | 2.50 |
| Glycerine | 16.75 |
| Water | 20.00 |
| Solid extract cornsilk | 15.00 |
| Propylene glycol | 33.38 |

Both Formulas A and B are useful in tobacco as flavor enhancers. They enhance the sweet, maple, nut-like character and enhance the natural smell of the tobacco. The tobacco blend on which the flavors are used contains:

| Ingredient | Amount |
|---|---|
| Virginia tobacco | 28% |
| Burley | 48% |
| Remaining tobaccos (Oriental, Turkish, stems, reconstituted tobacco) | 24% |

What is claimed is:

1. A 2-alkylidene-3-alkenal having the formula:

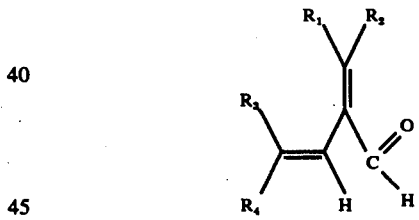

wherein one of $R_1$ and $R_2$ is hydrogen and the other is methyl and one of $R_3$ and $R_4$ is hydrogen and the other is an alkyl group containing two or four carbon atoms, selected from the group consisting of:
cis-2-ethylidene-trans-3-hexenal;
cis-2-ethylidene-cis-3-hexenal;
trans-2-ethylidene-trans-3-hexenal;
trans-2-ethylidene-6-methyl-cis-3-heptenal; and
trans-2-ethylidene-6-methyl-trans-3-heptenal.

2. A mixture consisting of 70% cis-2-ethylidene-cis-3-hexenal; 20% trans-2-ethylidene-cis-3-hexenal; and 10% diethyl acetal of cis-2-ethylidene-cis-3-hexenal.

3. The compound of claim 1 which is cis-2-ethylidene-trans-3-hexenal.

4. The compound of claim 1 which is cis-2-ethylidene-cis-3-hexenal.

5. The compound of claim 1 which is trans-2-ethylidene-trans-3-hexenal.

6. The compound of claim 1 which is trans-2-ethylidene-6-methyl-cis-3-heptenal.

7. The compound of claim 1 which is trans-2-ethylidene-6-methyl-trans-3-heptenal.

* * * * *